(12) United States Patent
Bartlett

(10) Patent No.: US 6,635,074 B2
(45) Date of Patent: Oct. 21, 2003

(54) SUTURE ANCHOR AND ASSOCIATED METHOD OF IMPLANTATION

(76) Inventor: Edwin C. Bartlett, 609 Bremerton Dr., Greenville, NC (US) 27858

(*) Notice: Subject to any disclaimer, the term of this patent is extended or adjusted under 35 U.S.C. 154(b) by 188 days.

(21) Appl. No.: 09/941,527

(22) Filed: Aug. 29, 2001

(65) Prior Publication Data

US 2002/0007196 A1 Jan. 17, 2002

Related U.S. Application Data

(62) Division of application No. 09/390,715, filed on Sep. 7, 1999, now Pat. No. 6,306,158.
(60) Provisional application No. 60/122,355, filed on Mar. 2, 1999.

(51) Int. Cl.[7] ............................................. A61B 17/04
(52) U.S. Cl. ....................................................... 606/232
(58) Field of Search ......................................... 606/232

(56) References Cited

U.S. PATENT DOCUMENTS

| | | |
|---|---|---|
| 4,669,473 A | 6/1987 | Richards et al. |
| 4,946,468 A | 8/1990 | Li |
| 5,085,661 A | 2/1992 | Moss |
| 5,102,421 A | 4/1992 | Anspach, Jr. |
| 5,203,787 A | 4/1993 | Noblitt et al. |
| 5,207,679 A | 5/1993 | Li |
| 5,258,016 A | 11/1993 | DiPoto et al. |
| 5,269,809 A | 12/1993 | Hayhurst et al. |
| 5,354,298 A | 10/1994 | Lee et al. |
| 5,405,359 A | 4/1995 | Pierce |
| 5,423,860 A | 6/1995 | Lizardi et al. |
| 5,464,425 A | 11/1995 | Skiba |
| 5,522,844 A | 6/1996 | Johnson |
| 5,540,718 A | 7/1996 | Bartlett |
| 5,584,835 A | 12/1996 | Greenfield |
| 5,626,612 A | 5/1997 | Bartlett |
| 5,626,613 A | 5/1997 | Schmieding |
| 5,647,874 A | 7/1997 | Hayhurst |
| 5,683,401 A | 11/1997 | Schmieding et al. |
| 5,683,418 A | 11/1997 | Luscombe et al. |
| 5,709,708 A | 1/1998 | Thal |
| 5,782,862 A | 7/1998 | Bonutti |
| 5,782,863 A | 7/1998 | Bartlett |
| 5,814,051 A | 9/1998 | Wenstrom, Jr. |
| 5,814,070 A | 9/1998 | Borzone et al. |
| 5,814,071 A | 9/1998 | McDevitt et al. |
| 5,814,072 A | 9/1998 | Bonutti |
| 5,814,073 A | 9/1998 | Bonutti |
| 5,868,789 A | 2/1999 | Huebner |
| 5,879,372 A | 3/1999 | Bartlett |

FOREIGN PATENT DOCUMENTS

| | | |
|---|---|---|
| WO | WO 95/08295 | 3/1995 |
| WO | WO 97/37595 | 10/1997 |

OTHER PUBLICATIONS

PCT Notification of Transmittal of the International Search Report or the Declaration, mailed Mar. 28, 2000, International Application No. PCT/US99/29929, International Filing Date Dec. 15, 1999.

*Primary Examiner*—Gary Jackson
(74) *Attorney, Agent, or Firm*—Alston & Bird LLP

(57) ABSTRACT

A suture anchor is provided comprising a generally quadrilaterally shaped body having a bore-abutting surface with a leading gripping edge at one end of the bore-abutting surface, a trailing gripping edge at the other end, and a closing surface having an arcuate portion and a linear portion engaging the leading and trailing gripping edges, respectively, generally opposite the bore-abutting surface. The body further defines a suture bore extending transversely therethrough and an inserter bore adapted to receive an insertion tool. A suture engages the suture anchor through the bore and is adapted to engage bodily tissue to be secured to the bone. Also provided are a knotless suture anchor configuration, an associated insertion tool, and a suture anchor kit, as well as a method of implanting a suture anchor in a bore in a bone.

20 Claims, 9 Drawing Sheets

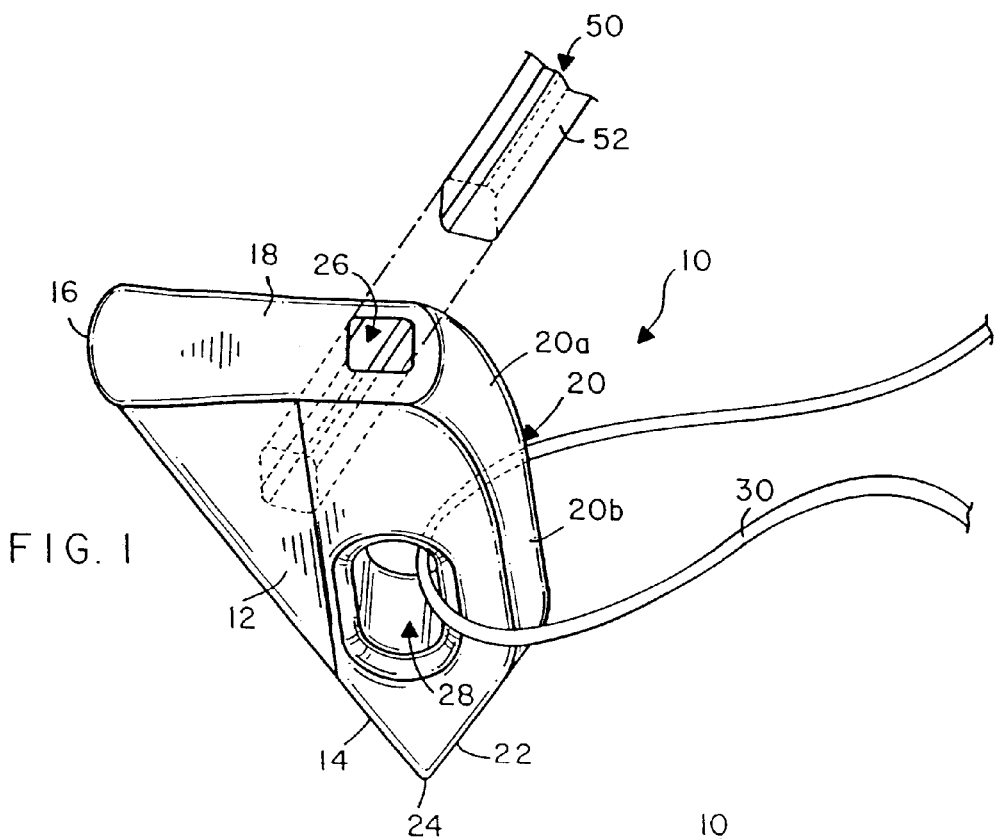
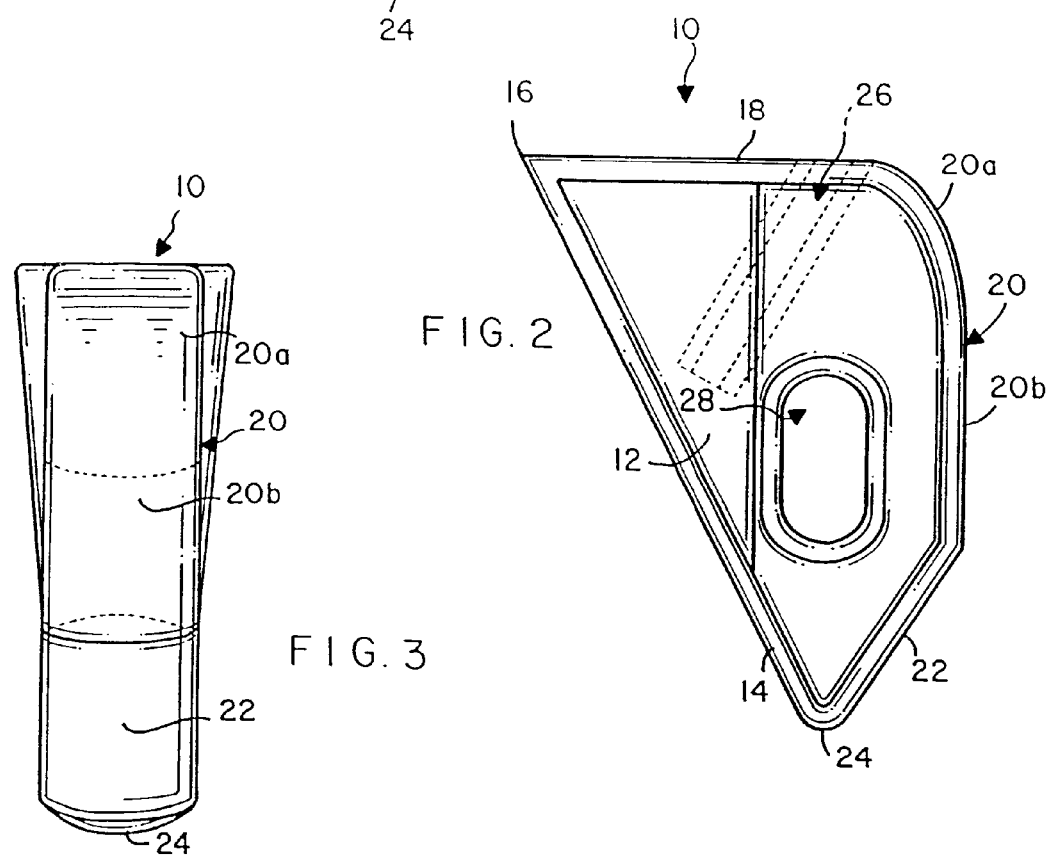

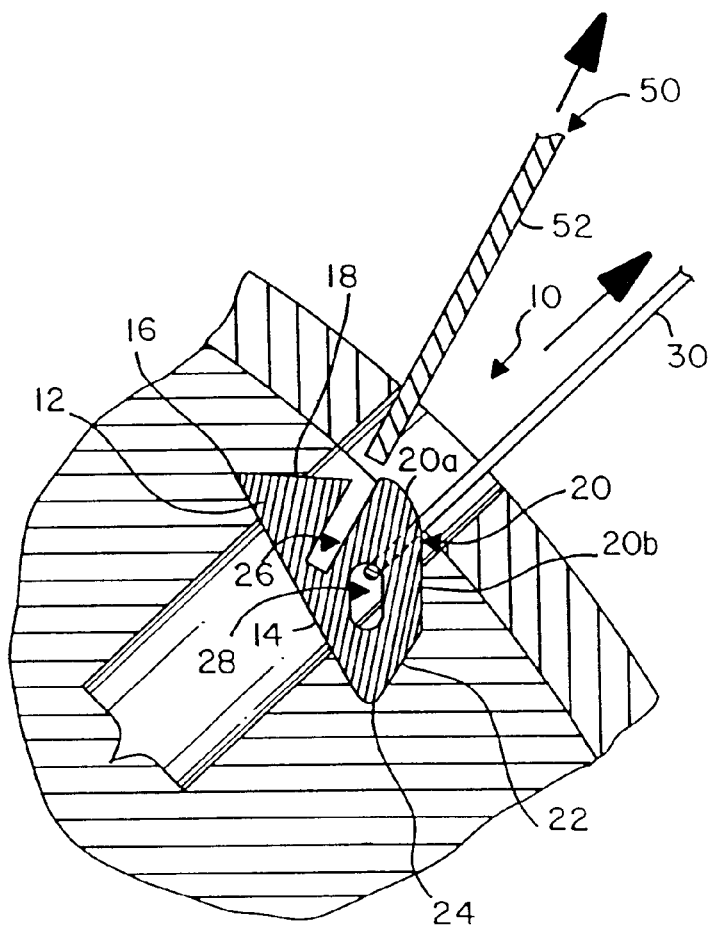
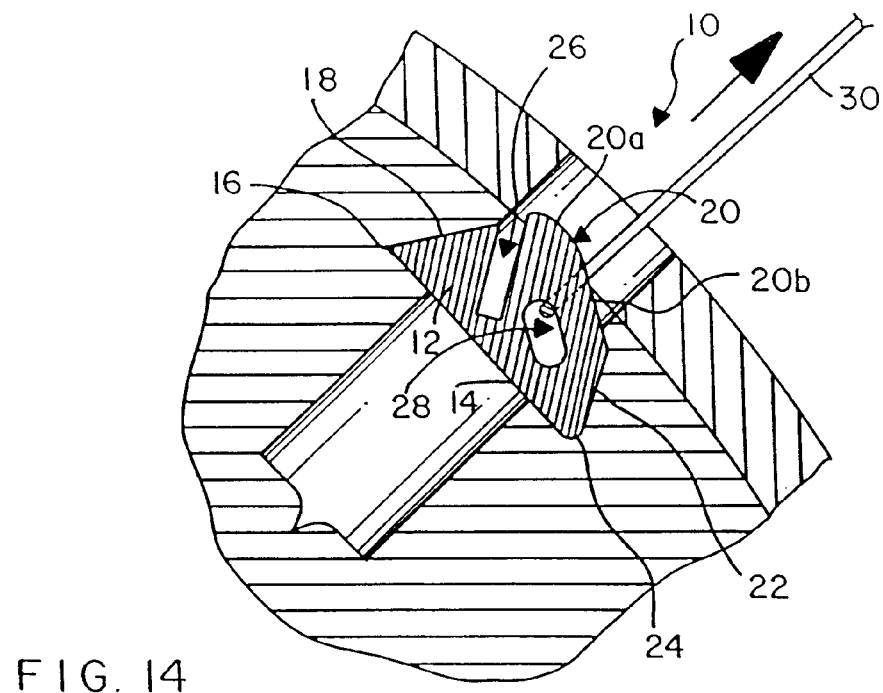
FIG. 13
FIG. 14

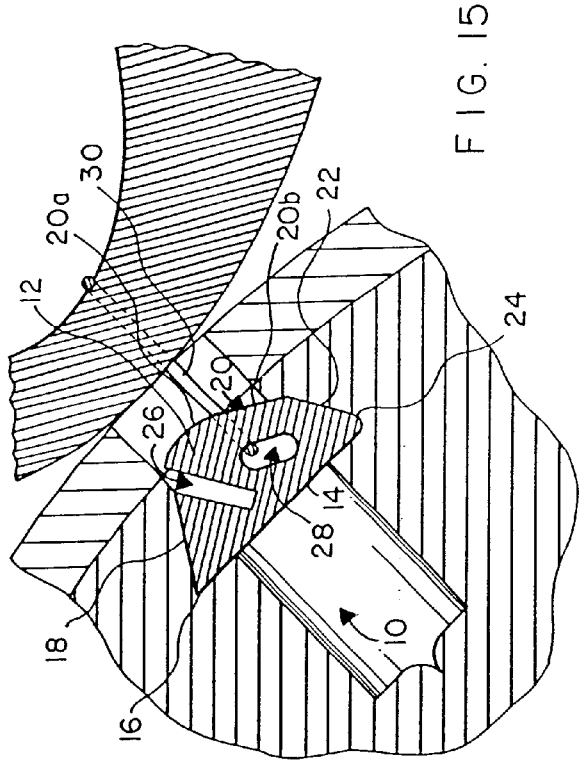
FIG. 15
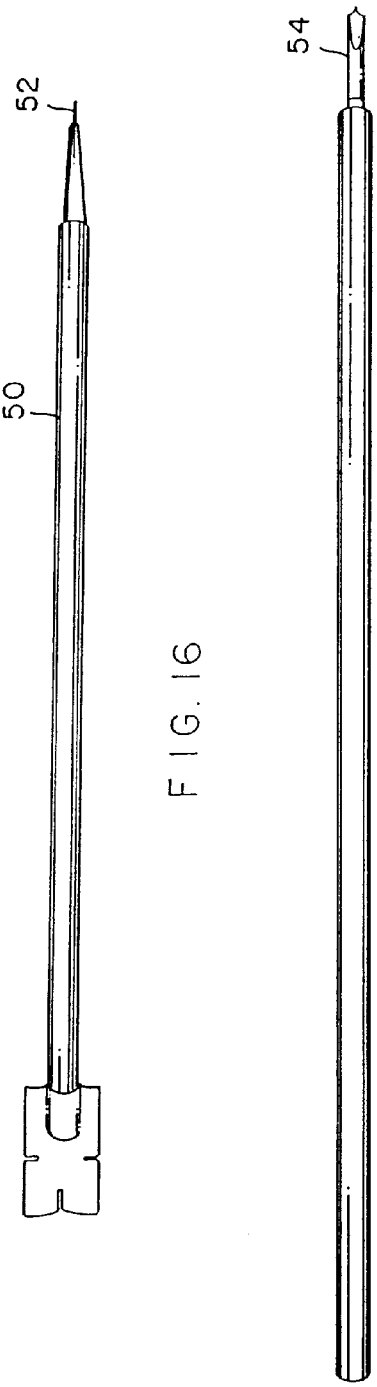
FIG. 16
FIG. 17

SUTURE ANCHOR AND ASSOCIATED METHOD OF IMPLANTATION

CROSS-REFERENCE TO RELATED APPLICATIONS

This application is a divisional of U.S. application Ser. No. 09/390,715, filed Sep. 7, 1999, now U.S. Pat. No. 6,306,158, which claims the benefit U.S. Provisional Application No. 60/122,355, filed Mar. 2, 1999, each of which is hereby incorporated herein in its entirety by reference.

FIELD OF THE INVENTION

The present invention relates to surgical implements and, more particularly, to suture anchors for enabling sutures to be attached to bone.

BACKGROUND OF THE INVENTION

Certain injuries or conditions within the human body often require that bodily tissue be firmly affixed to an adjacent bone structure to secure the tissue in a desired position, for instance, where a ruptured tendon must be reattached to the corresponding bone. To this end, suture anchors have been developed, providing an anchor in the bone to which a suture may be secured, wherein the suture is then used to secure the adjacent bodily tissue. Suture anchors generally are inserted into a bore formed in the bone. There are several types of suture anchors in the prior art, including a barb-type anchor, a corkscrew type anchor, an insert type anchor with offset reorienting suture bore, and a wedge-type anchor. Of these types of suture anchors, the wedge-type anchor has shown good promise.

In practice, wedge-type anchors with attached sutures are first introduced with an insertion tool into a bore drilled into the bone at a location where the bodily tissue must be affixed. The suture anchor generally includes a first gripping portion, such as a sharp edge or a point, and is designed to rotate as it enters the bore or is in the process of being withdrawn therefrom. As the suture anchor rotates, the first gripping portion bites or penetrates the wall of the bore and causes further rotation of the anchor. At the opposite end of the suture anchor, a second gripping portion is typically provided. The second gripping portion penetrates into the wall of the bore generally opposite the first gripping portion as the suture anchor is rotated, thereby wedging the suture anchor within the bore. When the suture anchor has rotated about the first gripping portion as much as the second gripping portion will allow with respect to the bone structure surrounding the bore, the suture anchor is in its seated position where it is anchored in the bore and ready to have adjacent bodily tissue attached thereto.

However, while suture anchors are theoretically designed to work with all bones, the structure of bone can vary greatly depending on the area of the body in which the suture anchor is required. Bones generally include a number of trabeculae disposed throughout. The spacing of the trabeculae within the intermedulary canal of the bone is often a good indicator of the density of the bone. Cortical bone is solid bone without visible interstitial spaces and is typical of the midshafts, or diaphyseal regions, of long bones. Metaphyseal and epiphyseal bone, which is the bone around the joints at the opposing ends of the long bones, has a variable amount of cortical shells with a deeper trabecular structure, wherein the amount of cortical shells may vary greatly. Dense bone typically has small and closely spaced trabeculae, resulting in a hard and strong bone. In comparison, less dense or osteoporotic bone has larger and more widely spaced trabeculae, typically resulting in a softer and generally weaker bone. This less dense bone generally comprises a cancellous bone region about the intermedulary canal. A typical bone structure thus typically includes a cortical layer atop cancellous layer where the proportion of both types of bone may vary. Since the structure of bone may vary significantly from one area of the body to another, the specific performance characteristics required of a suture anchor also vary accordingly. Therefore, suture anchors must be able to function as intended when used in all types of bone structure. Where suture anchors are implanted into dense bone structures, well defined strong gripping edges are required for the suture anchor to securely engage the bore in the bone. However, where the suture anchor is implanted into less dense bone, a large surface area engaging the bone is preferred in order to distribute and reduce the stresses on the relatively weak bone.

Examples of wedge-type suture anchors are found in U.S. Pat. Nos. 5,540,718, 5,626,612, 5,782,863, and 5,879,372 to Bartlett which disclose wedge-type suture anchors based on variants of cone, double cone, and combination cone and cylinder configurations. Additionally, U.S. Pat. No. 5,683,418 to Luscombe et al. assigned to Mitek Surgical Products, Inc., also the assignee of the present invention, discloses wedge-type suture anchors generally varying in shape from triangle to a quadrilateral. Thus, U.S. Pat. Nos. 5,540,718, 5,626,612, 5,782,863, and 5,879,372 to Bartlett and U.S. Pat. No. 5,683,418 to Luscombe et al. are incorporated in their entirety herein by reference.

The Luscombe et al. '418 patent discloses suture anchors which are angularly shaped, generally approximating a triangle to a quadrilateral and having straight sides. The intersections of major surfaces defining the perimeter of the suture anchor therefore define sharp transitions. Thus, the device disclosed by the '418 patent is generally more useful in dense bone structures where the sharp gripping edges more effectively bite into the bore in the dense bone. However, with the sharp gripping edges biting into the bone, the '418 device generally experiences less rotation in both dense and less dense bone than is desirable to properly seat the anchor. Rotation is further inhibited by the long straight surfaces defining the device.

A possible additional limitation of the '418 device is that the insertion tool used for implanting the suture anchor in the bore is formed from a material having a frangible portion at or near the interface with the anchor which breaks or separates from the anchor after implantation thereof. I the alternative, the '418 device uses a metallic insertion tool which engages a bore in the anchor in a friction fit. Both insertion tools may experience problems in that the tool with the frangible portion may not provide enough strength for manipulating the anchor within the bore, while the friction fit tool may be difficult to separate from the anchor after implantation thereof.

The Bartlett '718, '612, '863, and '372 patents disclose wedge-type suture anchors based on variants of cone, double cone, and combination cone and cylinder configurations. These devices use the tip of the cone, or a truncation thereof, to form the edge which first bites into the bone and then provides the point about which the anchor rotates. However, with the reduced cross-sectional area at or near the tip of the cone, this main biting edge may be weaker and prone to breaking in high stress situations, such as where the anchor is being implanted in a dense bone structure. In addition, wedge-type suture anchors generally use a suture, engaged with the anchor through a bore therein, to assist in rotating and seating the anchor within the bone. The wedge-type suture anchors generally have the bore located between the main biting edge and the bore in which the insertion tool is inserted, thereby providing a small moment arm for rotating the suture anchor using the suture. Thus, the suture may be less helpful in assisting the suture anchor to rotate within the bore in the bone, especially in a dense bone structure where the anchor is more difficult to rotate. On the other hand, the Bartlett devices may be more effective in less dense bone where the main biting edge does not experience as high a stress during the seating process for the anchor. Further, the anchor may be able to rotate to a greater extent within the bore in a less dense bone, thus allowing the suture to be more effective in rotating and seating the anchor. Accordingly, since the Bartlett devices are able to rotate more extensively in less dense bone, the anchor can be more effectively seated, thus providing the greater surface area which is desirable for a suture anchor used in less dense bone.

Thus, there exists a need for a suture anchor which will effectively anchor a suture within a bore in a bone while also preferably functioning equally in bones of differing densities, from hard dense bone to softer, less dense bone.

SUMMARY OF THE INVENTION

The above and other needs are met by embodiments of the present invention which provide a suture anchor particularly adapted for effectively anchoring sutures in all types of bone structures from hard dense cortical bone to softer, less dense cancellous bone. In one embodiment the suture anchor comprises a body having a bore-abutting surface with a leading gripping edge at one end of the bore-abutting surface, a trailing gripping edge at the other end thereof, and a closing surface engaging the leading and trailing gripping edges generally opposite the bore-abutting surface. The body further defines a suture bore extending transversely therethrough and an inserter bore adapted to receive an insertion tool. A suture engages the suture anchor through the bore such that it is adapted to engage bodily tissue to be secured to the bone.

The suture anchor is preferably quadrilaterally shaped with the side having the longest dimension comprising the bore-abutting surface. A leading surface intersects one end of the bore-abutting surface at an acute angle to form the leading gripping edge. A trailing surface intersects the other end of the bore-abutting surface at an acute angle to form the trailing gripping edge. The configurations of both the leading and trailing gripping edges may be varied according to the structure of the bone in which the anchor is to be inserted. A closing surface having an arcuate portion and a substantially linear portion engages the ends of the leading and trailing surfaces, respectively, opposite the bore-abutting surface, to form a generally quadrilaterally shaped body. The body further defines a suture bore extending transversely therethrough and disposed adjacent the trailing gripping edge, wherein the suture bore may vary in size. The suture bore also engages a suture, wherein the suture passes through the suture bore and is adapted to engage bodily tissue adjacent the bore. In addition, in order to facilitate insertion of the suture anchor within the bore in the bone, the body defines an inserter bore adapted to receive an insertion tool. The inserter bore preferably extends through the leading surface such that it is angularly disposed with respect to the bore-abutting surface. More preferably, the inserter bore is disposed between the leading gripping edge and the suture bore and has a uniform cross-sectional shape along its length. The inserter bore preferably has a non-circular cross-section, where a generally square shape is most preferred.

The suture anchor may also be varied in size and configuration according to characteristics and structure of the bone in the affected area of the body and the performance characteristics required of the suture anchor. Preferably, the body of the suture anchor is comprised of a biocompatible material, with a bioabsorbable material being particularly desirable. The body may be comprised of, for instance, polylactic acid, polydioxanone, polyglycolic acid, or the like, with polylactic acid being most preferred.

A further advantageous aspect of the present invention comprises an alternate embodiment of a suture anchor configured to permit knotless sutures to be used to secure bodily tissue to the adjacent bone structure. The alternate knotless embodiment of the present invention comprises generally the same suture anchor configuration as the embodiments previously described, but further including a notch in the bore-abutting surface and a suture forming a loop through the suture bore. Preferably, the suture is adapted to engage the bodily tissue to be secured to the bone. Once the bodily tissue is engaged, the suture wraps back about the body and engages the notch. The body is then implanted into the bore in the bone to secure the bodily tissue thereto without requiring further knotting of the suture.

Still another advantageous aspect of the present invention comprises an insertion tool for inserting a suture anchor within a bore in a bone. The insertion tool generally comprises a rigid shaft having opposed ends with a tip engaged with one end of the shaft. The tip further has a proximal end operably engaged with the shaft and a distal end adapted to be engaged with an inserter bore in a suture anchor. The tip is preferably comprised of a shape memory material, such as a nickel-titanium alloy, with a non-circular cross-section corresponding to the cross-sectional shape of the inserter bore in the body. In addition, it is further advantageous for the tip to have a uniform cross-sectional shape along its length to facilitate ease of separation from the inserter bore. Further, a non-circular or, more particularly, a generally square shape of the tip minimizes rotation of the suture anchor about the axis of the tip. Thus, the use of a shape memory material for the tip, and a shape for the tip which inhibits rotation of the anchor with respect thereto, allows the tip to be small in size. The small size of the tip thereby allows the tool and the suture anchor to be more easily manipulated within the bore and allows for small-sized suture anchors.

Yet a further advantageous aspect of the present invention comprises a kit for anchoring a suture in a bore in a bone. According to one embodiment, the kit comprises at least one insertion tool and at least one suture anchor according to the previously described embodiments thereof. At least one boring bit may also be included, with the bit capable of forming a bore of sufficient size in a bone to accommodate a provided suture anchor.

Another advantageous aspect of the present invention comprises a method of implanting a suture anchor within a bore in a bone. A suture anchor is first urged into engagement with the bore using an insertion tool angled with respect to the bore such that a bore-abutting surface of the suture anchor is engaged with the wall of the bore. The insertion tool is then elastically deformed to urge the suture anchor into the bore such that the bore-abutting surface remains engaged with the wall of the bore as the suture anchor is inserted. The suture anchor is then manipulated within the bore by moving the insertion tool to the diametrically opposite side of the bore such that the suture anchor rotates about a leading gripping edge thereof. After the insertion tool is removed from the suture anchor, the suture anchor is further rotated into a seated position within the bore by the exertion of a tensile force on the suture passing through the suture bore. The suture anchor thus further rotates about the leading gripping edge, for example, up to about 90 degrees from its insertion angle, such that both the leading gripping edge and a trailing gripping edge are engaged with the wall of the bore. The suture anchor attains a seated position when the engagement of the trailing gripping edge with the wall of the bore prevents further rotation of the suture anchor.

Therefore, according to embodiments of the present invention, the leading gripping edge formed by the intersection of two surfaces provides a more robust structure than the tip of a cone, thereby providing a stronger suture anchor for high stress situations such as implantation of the anchor in high density bone. Further, the arcuate transition between the leading and trailing gripping edges facilitates rotation of the suture anchor in a bore in various bone structures, from dense cortical structures to less dense cancellous structures, thereby improving the seating ability of the suture anchor and requiring less effort to achieve the necessary rotation. In addition, the trailing gripping edge formed by the intersection of two surfaces provides a sharp gripping edge which is desirable in a dense bone structure. However, when included with the closing surface having an arcuate portion, the sharp trailing gripping edge permits the suture anchor to engage the bore in a less dense bone structure after the anchor has been rotated to provide the high seating surface area which is desirable for a less dense bone structure. Thus, the suture anchor according to embodiments of the present invention provides a mechanism for effectively anchoring a suture within a bore in a bone while also functioning equally in bones of differing densities, from hard dense bone to softer, less dense bone. Further, the uniform non-circular configuration of the inserter bore/insertion tool interface minimizes rotation of the suture anchor about the axis of the tip while facilitating a robust and easily connectable/disconnectable interface between the insertion tool and the suture anchor.

BRIEF DESCRIPTION OF THE DRAWINGS

Some of the advantages of the present invention having been stated, others will appear as the description proceeds, when considered in conjunction with the accompanying drawings, which are not necessarily drawn to scale, in which:

FIG. 1 is a perspective view of one embodiment of the present invention showing a suture anchor engaging a suture and corresponding insertion tool.

FIG. 2 is a lateral view of the embodiment of the present invention as shown in FIG. 1.

FIG. 3 is a rear view of one embodiment of the present invention as shown in FIG. 1.

FIGS. 7–14 show a cross-sectional sequence of insertion of a suture anchor into a bore in a bone in accordance with embodiments of the present invention.

FIG. 15 is a cross-sectional view of bodily tissue being attached to the bone by a suture anchored within the bone by a suture anchor in accordance with an embodiment of the present invention.

FIG. 16 shows an insertion tool for inserting a suture anchor into a bore in a bone according to one embodiment of the present invention.

FIG. 17 shows a boring tool for forming a bore in a bone in which a suture anchor is implanted according to one embodiment of the present invention.

DETAILED DESCRIPTION OF THE INVENTION

Figure 4:
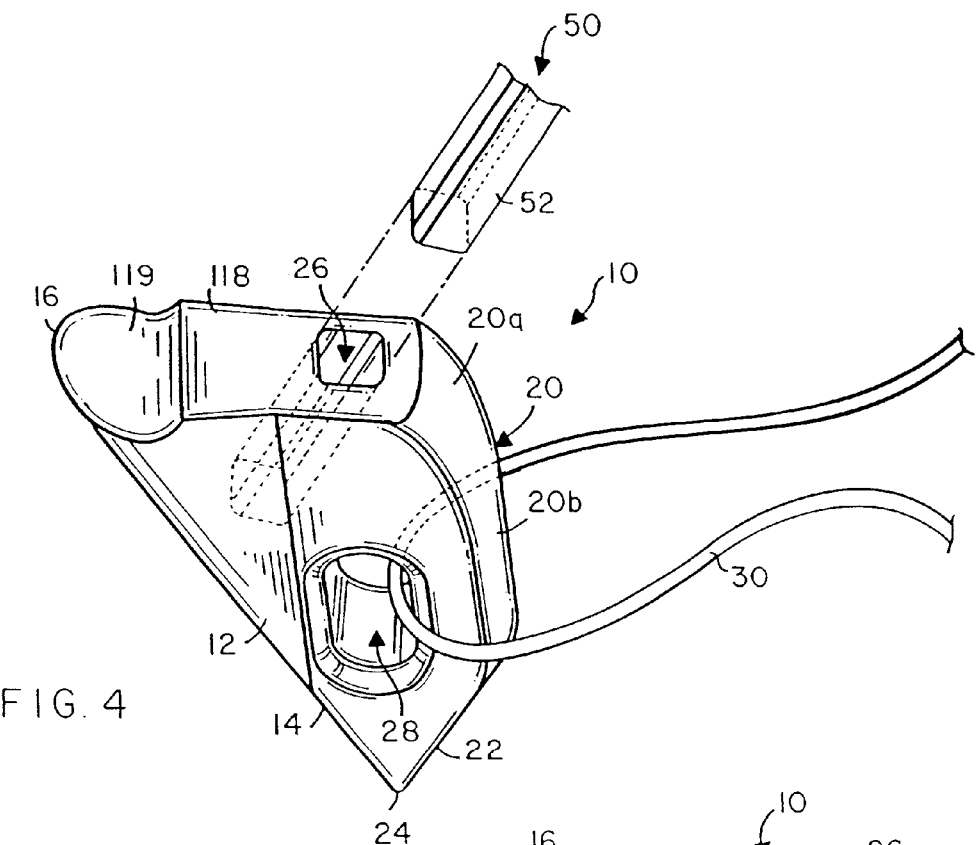
FIG. 4 is a perspective view of an alternate embodiment of the present invention showing a suture anchor engaging a suture and corresponding insertion tool.

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

FIGS. 1–3 disclose one embodiment of the suture anchor according to the present invention, indicated generally by the numeral 10. The suture anchor 10 is preferably biocompatible and comprised of a bioabsorbable material, such as polylactic acid, polydioxanone, polyglycolic acid, and similar materials or blends thereof. Such materials should preferably be recognized by the appropriate regulatory authority as being suitable for use in humans. Additionally, it is desirable that the material strengthen the bone into which the anchor is inserted. It is further desirable for the material to be translucent or transparent to noninvasive examinations such as radiographs (e.g., X-rays). Accordingly, the suture anchor may also be comprised of cortical bone, where the bone may further be autologous or autogenous bone. Generally, the suture anchor may be comprised of a suitable biocompatible polymer, biocompatible metal, or other biocompatible material (see, e.g., U.S. Pat. Nos. 5,540,718, 5,626,612, 5,782,863, and 5,879,372 to Bartlett and U.S. Pat. No. 5,683,418 to Luscombe et al.). The suture anchor 10 is generally quadrilaterally shaped and comprises a body 12 having a bore-abutting surface 14, a leading gripping edge 16, a leading surface 18, a closing surface 20, a trailing surface 22, a trailing gripping edge 24, an inserter bore 26, and a suture bore 28. The bore-abutting surface 14 and the leading surface 18 intersect at an acute angle to form the leading gripping edge 16. At the other end, the bore-abutting surface 14 intersects with the trailing surface 22 at an acute angle to form the trailing gripping edge 24. The leading surface 18 and the trailing surface 22 are further connected by the closing surface 20, dispose generally opposite the bore-abutting surface 14 and comprising an arcuate portion 20a and a substantially linear portion 20b. The body 12 further defines an inserter bore 26 in the leading surface 18 and a transverse suture bore 28 therethrough and through which a suture 30 is passed.

According to one embodiment of the present invention, the bore-abutting surface 14 may be a flat surface in both the longitudinal and lateral directions, but is preferably flat in the longitudinal direction and curved or radiused in the lateral direction along the edge of the body 12. The body 12 may also widen as it approaches the leading gripping edge 16 such that the leading gripping edge 16 is generally the widest portion of the body 12. Accordingly, both the bore-abutting surface 14 and the leading surface 18 are wider approaching the leading gripping edge 16. The leading gripping edge 16 is preferably wide in order to distribute the anchoring stress over a greater surface area, as well as to strengthen the suture anchor 10, as is further explained herein. The leading surface 18 is generally a flat surface and defines the inserter bore 26. The inserter bore 26 is preferably located in the leading surface 18 in the vicinity where the leading surface 18 meets the arcuate portion 20a of the closing surface 20. The inserter bore 26 extends into the body 12 towards the bore-abutting surface 14, thereby forming an acute angle with the leading surface 18.

The inserter bore 26 is preferably configured to receive the tip 52 of an insertion tool 50 for implanting the suture anchor 10 within the bone. Preferably, the inserter bore 26 and the tip 52 have corresponding non-circular lateral cross-sections, wherein the cross-sectional shapes are uniform along the lengths thereof. Preferably, the tip 52 of the insertion tool 50 is generally square, but may have beveled or radiused corners, and the inserter bore 26 is accordingly shaped to receive the tip 52. Generally, the tip 52 of the insertion tool 50 may be any shape or configuration which minimizes rotation of the suture anchor 10 about the longitudinal axis of the tip 52. In addition, at least the tip 52 of the insertion tool 50 is preferably formed from a material having elastic properties and, more preferably, superelastic properties, such as a shape memory material. The elastic or superelastic properties of the material should be such that the tip 52 is not substantially permanently deformed during insertion and implantation of the suture anchor 10, thereby allowing the tip 52 to substantially return to an initial configuration (generally the configuration of the tip 52 as it is initially inserted into the inserter bore 26). Preferably, at least the tip 52 of the insertion tool 50 is comprised of a nickel-titanium alloy, such as is commercially available under the names NITINOL™ (Raychem), TINEL™ (Raychem), or SENTINOL™ (GAC International Inc.). Such shape memory alloys having superelastic properties are well known in the art; however, any other shape retaining material sufficient for properly implanting the suture anchor 10 of the present invention in a bore in a bone may be used. The use of a shape memory material and the shape of the tip 52 which minimizes rotation of the suture anchor 10 about the tip 52 engaged therewith further allows a smaller sized tip 52 to be used to effectively implant the suture anchor 10 within a bone. In addition, a smaller sized tip 52 further allows a smaller suture anchor 10 to be used in situations where such is necessary or desired.

According to one embodiment of the present invention, the suture anchor 10 may include a suture 30 engaged therewith through the suture bore 28. The suture bore 28 is disposed intermediate the bore-abutting surface 14 and the linear portion 20b of the closing surface 20, adjacent the trailing surface 22 and the trailing gripping edge 24. The suture bore 28 may vary in size and is preferably rounded or beveled around the openings in the body 12 in order to avoid abrasion of the suture 30. Most preferably, the suture bore 28 is disposed in the body 12 on the opposing side of the inserter bore 26 from the leading gripping edge 16. That is, the inserter bore 26 is most preferably disposed intermediate the leading gripping edge 16 and the suture bore 28. Since, as will be described further herein, the leading gripping edge 16 provides a point about which the suture anchor 10 is rotated by a tensile force applied to the suture 30 threaded through the suture bore 28, disposing the suture bore 28 adjacent the trailing gripping edge 24 provides a larger moment arm for exerting the necessary rotational force on the suture anchor 10 via the suture 30. Thus, more turning torque may be exerted on the suture anchor 10 as compared to a suture anchor 10 having the suture bore 28 disposed on the opposite side of the inserter bore 26 and closer to the leading gripping edge 16. The suture anchor 10 is typically rotated within the bore in the bone until a seated position is attained, wherein the seated position is preferably up to about ninety degrees from the orientation in which the suture anchor 10 was initially inserted into the bore. The degree of rotation depends, at least in part, on the structure of the bone into which the suture anchor 10 is implanted.

The closing surface 20 and the trailing surface 22 may be flat surfaces, but preferably are curved or radiused in the lateral direction for the lengths thereof. As described further herein in accordance with a preferred method of the present invention, the inserter bore 26 cooperates with an insertion tool 50 to introduce the suture anchor 10 into a bore in a bone. As the suture anchor 10 is introduced into the bore, the bore-abutting surface 14 lies flush with the wall of the bore, with the insertion tool 50 forcing it thereagainst. The closing surface 20 and, more specifically, the arcuate portion 20a defining the maximum width of the suture anchor 10 as measured perpendicularly from the bore-abutting surface 14, is disposed adjacent the wall of the bore diametrically opposite the leading gripping edge 16. Thereafter, moving the insertion tool 50 to the diametrically opposite side of the bore or applying a tensile force on the suture 30 outwardly of the bore tends to cause the suture anchor 10 to rotate such that the leading gripping edge 16 is driven into the wall of the bore. Thus, the rotation of the suture anchor 10 is preferably initiated by moving the insertion tool 50 to the diametrically opposite side of the bore from which the insertion tool 50 initially introduced the anchor 10 into the bore. Once the insertion tool 50 is removed from the inserter bore 26, tensile force on the suture 30 is used complete the rotation of the anchor 10 into a seated position.

The arcuate portion 20a of the closing surface 20 facilitates rotation of the suture anchor 10 about the leading gripping edge 16 as the insertion tool 50 is moved to the opposite side of the bore and/or a tensile force is applied to the suture 30. As the suture anchor 10 is further rotated by the insertion tool 50 and/or the tensile force applied to the suture 30, the rotation of the suture anchor 10 continues until the intersection of the linear portion 20b of the closing surface 20 and the trailing surface 22 and/or the trailing gripping edge 24 begins to penetrate the wall of the bore opposite the leading gripping edge 16. However, once the insertion tool 50 is removed from the inserter bore 28, the rotation of the suture anchor 10 into the seated position is accomplished solely by exerting tensile force on the suture 30.

Figure 5:
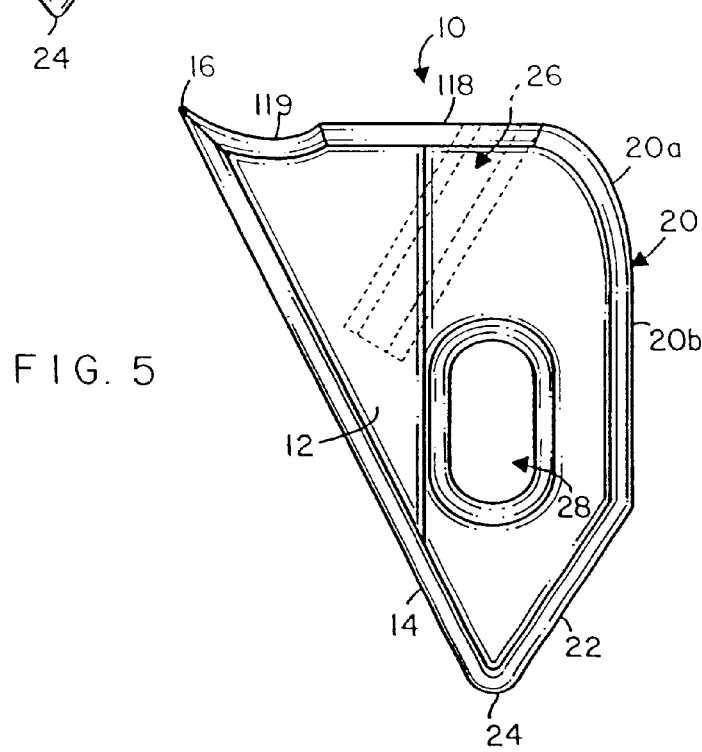
FIG. 5 is a lateral view of the alternate embodiment of the present invention as a shown in FIG. 4.

An alternate embodiment of the present invention is shown in FIGS. 4 and 5. While generally similar to the embodiments as described above, this alternate embodiment differs in the configuration of the leading surface 118. Here, the leading surface 118 further comprises a concave depression 119 therein immediately prior to intersection of the leading surface 118 and the bore-abutting surface 14. The concave depression 119 thus redefines the leading gripping edge 16 as a scoop since it forms a more acute angle between the bore-abutting surface 14 and the leading surface 118.

Figure 6:
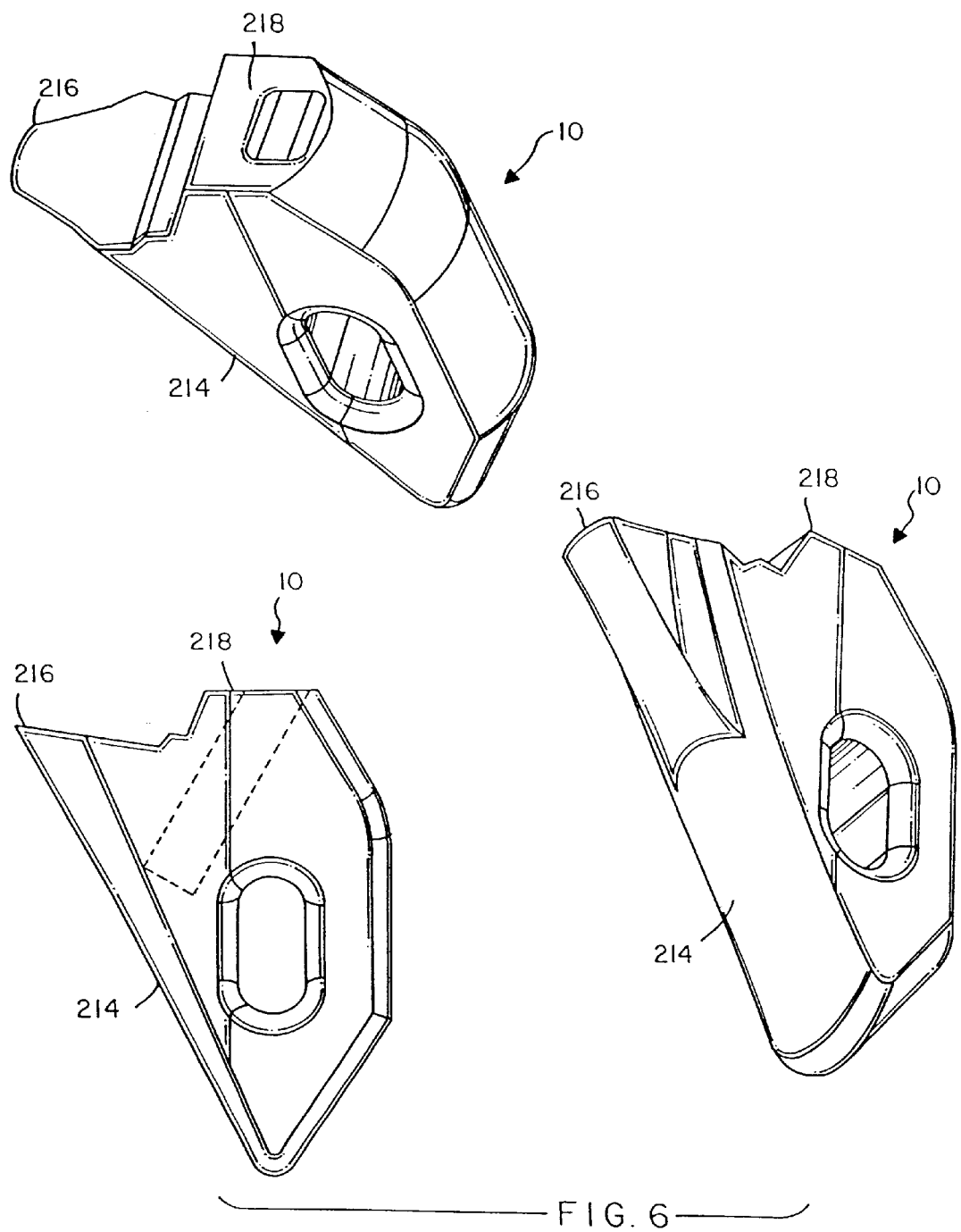
FIG. 6 shows multiple views of still another alternate embodiment of the present invention.
Figure 6A:
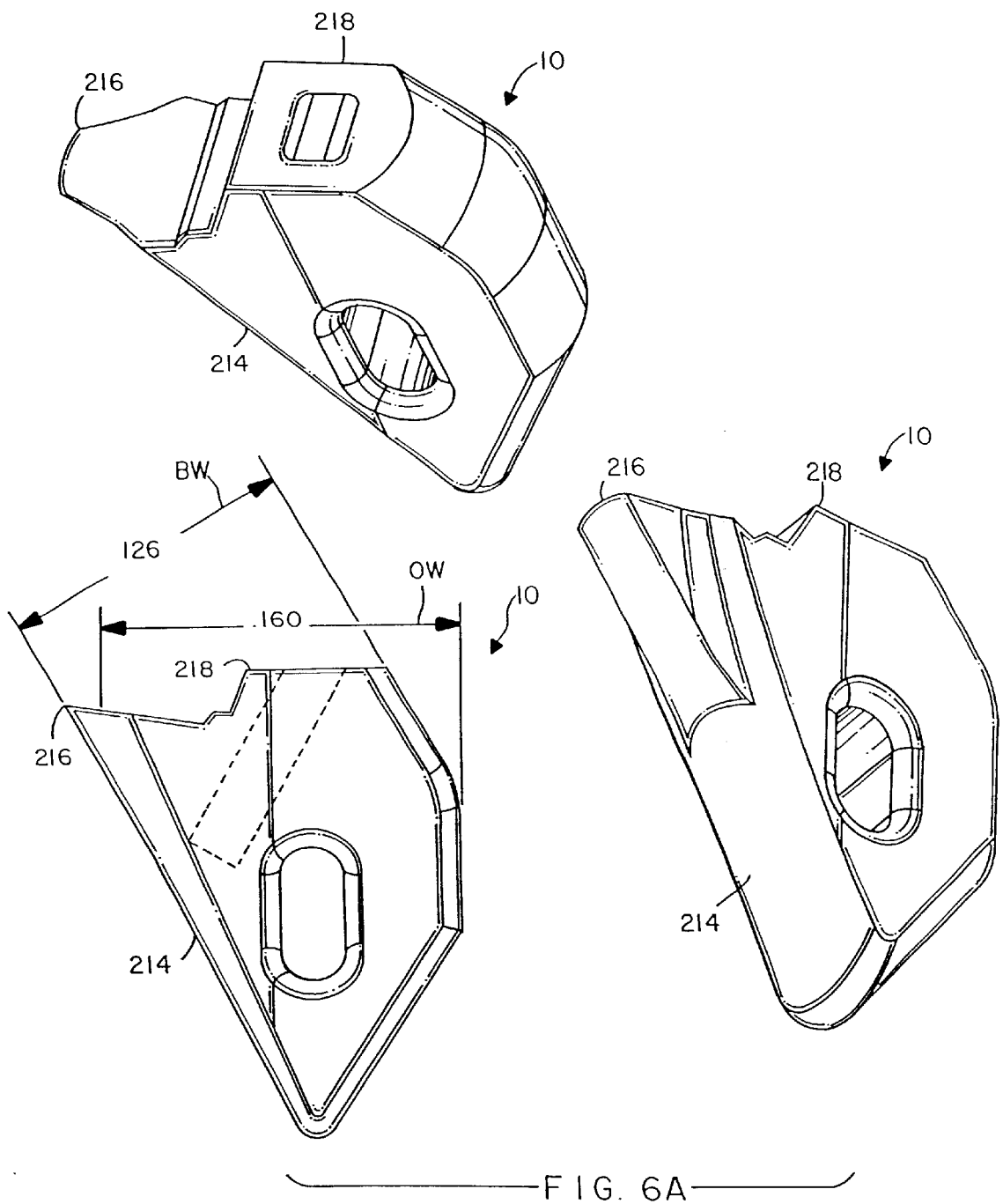
FIG. 6A shows multiple views of yet another alternate embodiment of the present invention.

Further alternate embodiments of the present invention are shown in FIGS. 6 and 6A. As shown in FIG. 6, the leading surface 218 is downwardly stepped between the inserter bore 26 and the leading gripping edge 216. Further, the bore-abutting surface 214 varies in width as it intersects the leading surface 218, thereby forming a reduced width leading gripping edge 216. A reduced width leading gripping edge 216 may be advantageous, for example, in dense bone structures where biting of the leading gripping edge 216 into the wall of the bore may be facilitated by a smaller and sharper structure. As further shown in FIG. 6A, various dimensions of the suture anchor 10 may be varied according to the performance characteristics desired for the particular application. For example, the increased dimensions BW and OW produce a larger and more robust suture anchor 10, which further requires a larger bore in the bone into which it is inserted. These characteristics may be advantageous where, for instance, larger bone structures are involved and/or it is anticipated that the bodily tissue to be fastened to the bone will experience higher stresses at the attachment thereto. In this instance, a larger and stronger suture anchor 10 may be desirable. Thus, in embodiments of the present invention, the dimensions and configurations of the suture anchor 10 may be varied to adapt the suture anchor 10 to the requirements of the particular application.

Figure 7:
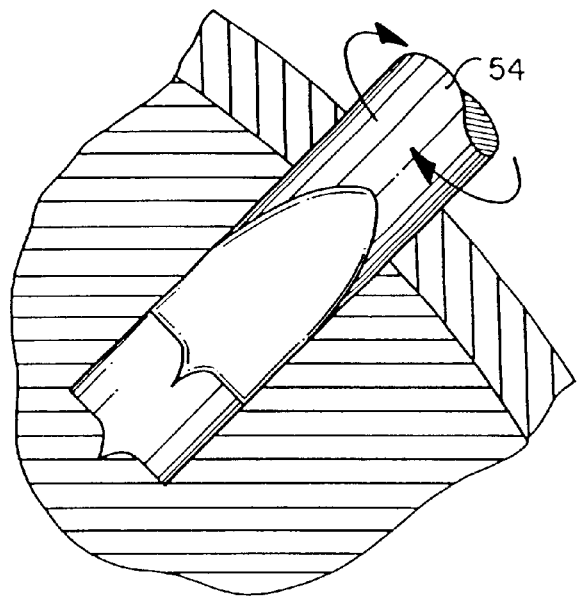
Figure 8:
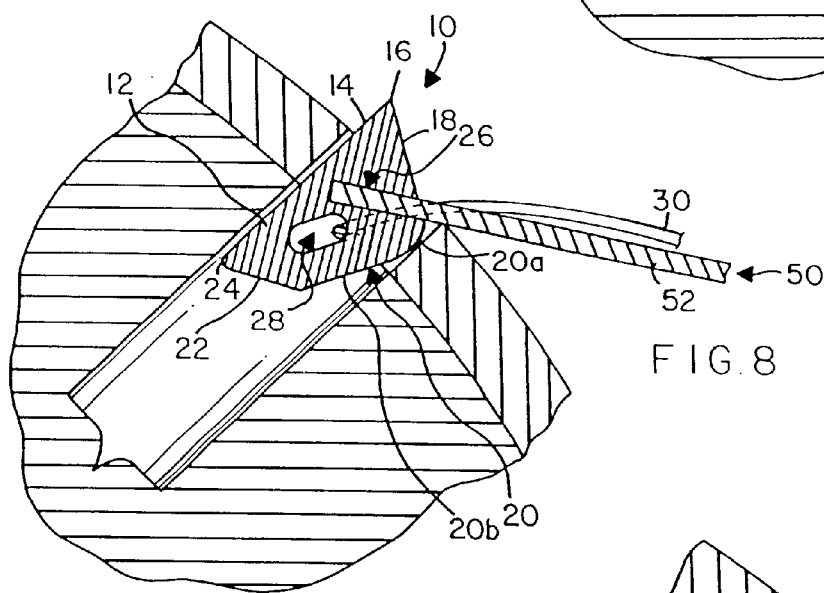

In accordance with embodiments of the present invention, a method of implanting the suture anchor 10 in a bore in a bone is shown in FIGS. 7–14. As shown in FIG. 7, a bore is first drilled in the bone using a boring bit 54. The bore generally passes through an outer layer of dense bone (cortical layer) and into an inner layer of a less dense or osteoporotic bone (cancellous layer) further therein. Once the bore is formed, the boring bit 54 is removed. A suture anchor 10 is then prepared for insertion by inserting the tip 52 of an insertion tool 50 into the inserter bore 26. In addition, the suture anchor 10 typically includes a suture 30 threaded through the suture bore 28. After the tip 52 is inserted into the inserter bore 26, the loose ends of the suture 30 are attached to the insertion tool 50 in order to secure the suture 30 and prevent it from becoming tangled or damaged during the insertion process. As shown in FIG. 8, the suture anchor 10 is then introduced into the bore such that the bore-abutting surface 14 is engaged with the wall of the bore. In this position, the insertion tool 50 is in its original configuration (substantially straight), with the tip 52 inserted in the inserter bore 26 and angled with respect to the axis of the bore. Further, as shown, the diameter of the bore roughly corresponds to the maximum width of the suture anchor 10, defined as the maximum perpendicular dimension from the bore-abutting surface 14. This maximum width of the suture anchor 10 is roughly along the portion of the body 12 corresponding to the arcuate portion 20a of the closing surface 20. Thus, when the suture anchor 10 is introduced into the bore in the bone, the bore-abutting surface 14 is preferably contacting the wall of the bore, while the point defining the maximum width of suture anchor 10 (the arcuate portion 20a) is at least within close proximity to the wall of the bore diametrically opposite the bore-abutting surface 14.

Figure 9:
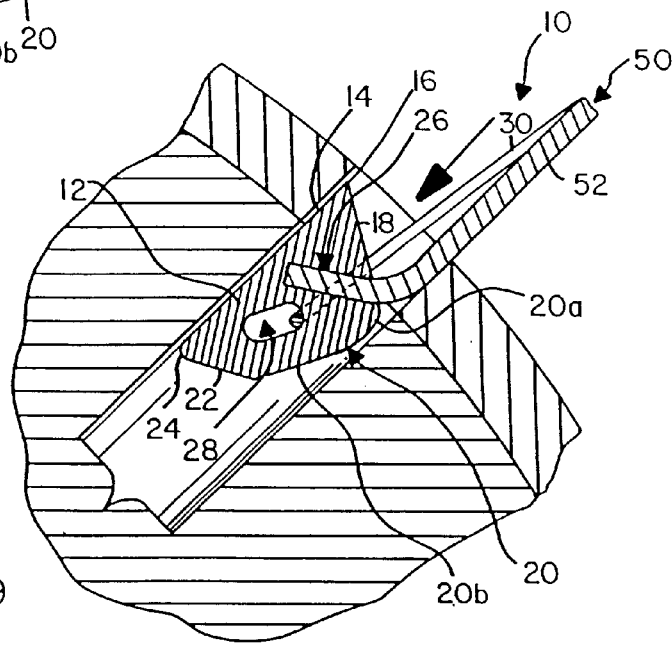

As shown in FIG. 9, a force directed inwardly with respect to the bore is then exerted on the insertion tool 50 such that the suture anchor 10 is urged into the bore. When the insertion tool 50 encounters the outer layer of cortical bone, the force causes the insertion tool 50 to bend such that distal end of the tip 52 remains in the inserter bore 26, but the portion of the tip 52 outside of the suture anchor 10 bends or deforms to conform to the wall of the bore. At this point, a portion of the bore-abutting surface 14 is still in contact with the dense cortical bone layer since suture anchor 10 has not been inserted far enough into the bore for the leading gripping edge 16 to pass by this bone layer. The bore-abutting surface 14, aided by the force provided by the tip 52 of the insertion tool 50, remains flush against the wall of the bore.

Figure 10:
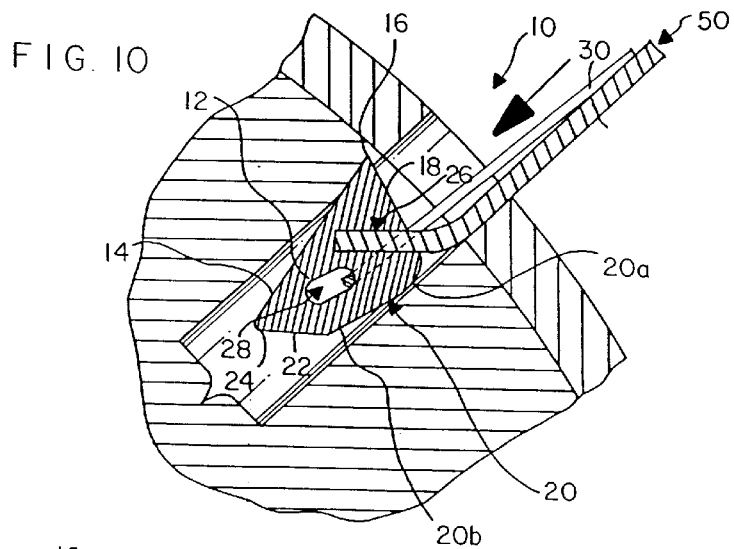
Figure 11:
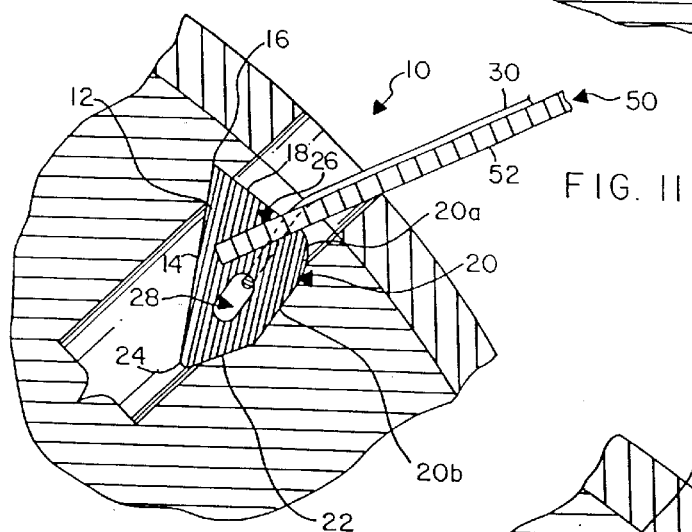

FIG. 10 shows the suture anchor 10 after further force has been exerted on the insertion tool 50 inwardly with respect to the bore. Once the suture anchor 10 has been inserted into the bore for a sufficient distance to clear the dense cortical surface layer of bone, it enters a less dense inner portion of the bone (the cancellous layer). Since the cancellous layer is less dense and weaker than cortical bone, the suture anchor 10 may begin to turn or rotate within the bore in response to force exerted by the tip 52 of the insertion tool 50 returning to its original shape due to the effect of the shape memory material from which it is comprised. As the rotation of the suture anchor 10 occurs, the leading gripping edge 16 is forced into the cancellous layer forming this portion of the wall of the bore. Diametrically opposed the leading gripping edge 16, the arcuate portion 20a is urged against the wall of the of the bore, wherein engagement with the wall proceeds along the arcuate portion 20a to the linear portion 20b and then to the trailing surface 22 as the suture anchor 10 rotates. Thus, the suture anchor 10 generally begins to rotate about the point where the leading gripping edge 16 engages the wall of the bore. As further shown in FIG. 11, the rotation of the suture anchor 10 may continue until the tip 52 of the insertion tool 50 has returned to its original shape such that the insertion tool 50 rests against the wall at the entrance to the bore. The suture anchor 10 has been illustrated in this method of implantation as interacting with a bone structure having a cancellous layer underlying a cortical layer, such as that found, for example, in the "rotator cuff" area of the human shoulder (also known as the greater tuberosity of the humorous). However, a suture anchor 10 according to embodiments of the present invention may also be used in areas of dense bone, predominantly comprised of a cortical layer with little or no underlying cancellous layer, such as, for example, at the "cup" or glenoid area of the shoulder. While the suture anchor 10 according to embodiments of the present invention may tend not to rotate as freely or extensively within a cortical bone layer as within a cancellous layer, it contains features further described herein which render the suture anchor 10 generally adapted for application to both dense cortical bone and less dense cancellous bone structures.

Figure 12:
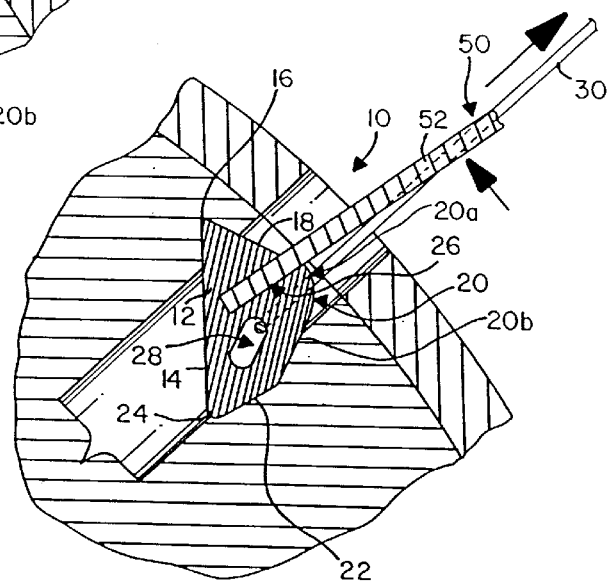

As shown in FIG. 12, further rotation of the suture anchor 10 may be obtained by exerting axial force on the suture 30 outwardly with respect to the bore and/or urging the insertion tool 50 to the diametrically opposite side of the bore. The forces exerted through the suture 30 and/or the insertion tool 50 causes the leading gripping edge 16 to bite or penetrate further into the wall of the bore and the suture anchor 10 to rotate thereabout. At the wall on the opposite side of the bore, the trailing gripping edge 24 begins to penetrate into the wall of the bore. FIG. 13 shows that rotation of the suture anchor 10 due to the force exerted on the suture 30 and/or the insertion tool 50 further brings the insertion tool 50 into contact with the wall on generally the opposite side of the bore from which the insertion tool 50 initially entered the bore. At this point, the insertion tool 50 is removed from the inserter bore 26 of the suture anchor 10 by a tensile force applied outwardly with respect to the inserter bore 26.

As shown in FIG. 14, once the insertion tool 50 is removed, further tensile force may be exerted on the suture 30 to complete the rotation of the suture anchor 10 within the bore to a seated position. In a seated position, the suture anchor 10 preferably may have rotated up to about ninety degrees from the orientation in which it was inserted into the bore. As shown in FIG. 14, in a cancellous bone layer, the suture anchor 10 in a seated position will preferably be disposed such that the bore-abutting surface 14 is substantially perpendicular to the axis of the bore. Both the leading gripping edge 16 and the trailing gripping edge 24 will have penetrated into the wall of the bore. Further, the divergence of the leading surface 18 from the trailing surface 22, as both approach the bore-abutting surface 14, increases the surface area of the suture anchor 10 engaging the bone in a seated position. Thus, in a less dense cancellous bone layer, the suture anchor 10, according to embodiments of the present invention, provides a large surface area over which a force exerted outwardly with respect to the bore can be distributed. Preferably, the size and configuration of the suture anchor 10 may be varied to provide an optimally effective surface area for the particular bone structure in which the suture anchor 10 is to be implanted. This feature is particularly advantageous where the cortical bone layer is relatively thin and does not significantly contribute to the strength of the bone. A suture anchor 10 having a large effective surface area in the seated position will distribute the stresses on a cancellous bone layer over a relatively larger area, thereby lowering the risk of the bone failing in the vicinity of the bore and thus the risk of the suture anchor 10 pulling out of the bone.

Where the suture anchor 10 is to be implanted in a bone having a dense cortical structure, the suture anchor 10 will not be able to rotate as extensively as in a cancellous bone structure since it is more difficult for the leading and trailing gripping edges 16 and 24 to penetrate the walls of the bore. In this situation, the suture anchor 10 according to embodiments of the present invention may be slightly smaller than the diameter of the bore. Thus, after the suture anchor 10 is inserted into the bore in the bone in the same manner as previously described, a tensile force applied to the suture 30, or a force resulting from the insertion tool 50 being urged toward the opposite side of the bore, causes rotation of the suture anchor 10. Since the bore is larger than the maximum width of the suture anchor 10, rotation of the suture anchor 10 within the bore is facilitated and the leading and trailing gripping edges 16 and 24 are better able to penetrate the wall of the bore to secure the suture anchor 10. Once the insertion tool 50 is removed from the suture anchor 10, a tensile force exerted on the suture 30 causes further rotation of the suture anchor 10 into a seated position within the bore in the cortical bone structure, where the degree of rotation is preferably up to about ninety degrees from the orientation in which the suture anchor 10 was inserted into the bore.

Once the suture anchor 10 has been implanted, the suture 30 engaged therewith through the suture bore 30 allows adjacent bodily tissue to be affixed to the bone, as shown in FIG. 15. For example, suture anchors 10 may be used in the pelvic region to provide attachment points for bladder suspension procedures, in the shoulder area for reattachment of the rotator cuff, or in the feet and/or knees to assist in reattaching tendons. Preferably, the suture anchor 10, according to embodiments of the present invention, is seated in the bore in the bone such that the anchoring force (the force required to extract a seated suture anchor 10 from the bore) approaches the tensile strength of the suture 30 threaded therethrough. Thus, according to one particularly advantageous embodiment, the suture anchor 10 and attached suture 30 may withstand a force of up to about 30 pounds without the suture anchor 10 pulling out of the bore or the suture 30 breaking. Generally, a minimum amount of tools are required for applying the suture anchors 10 according to embodiments of the present invention. As shown in FIGS. 16 and 17, typical tools used for applying the suture anchor 10 include an insertion tool 50 having a tip 52 comprised of a shape memory material as shown in FIG. 16 and a boring bit 54 as shown in FIG. 17. Accordingly, an advantageous aspect of the present invention may comprise a kit having at least one of a suture anchor 10, at least one of a corresponding boring bit 54, and at least one of a corresponding insertion tool 50, thus facilitating selection of an appropriate configuration of a suture anchor 10 for the particular bone structure in which it is to be implanted.

Figure 18:
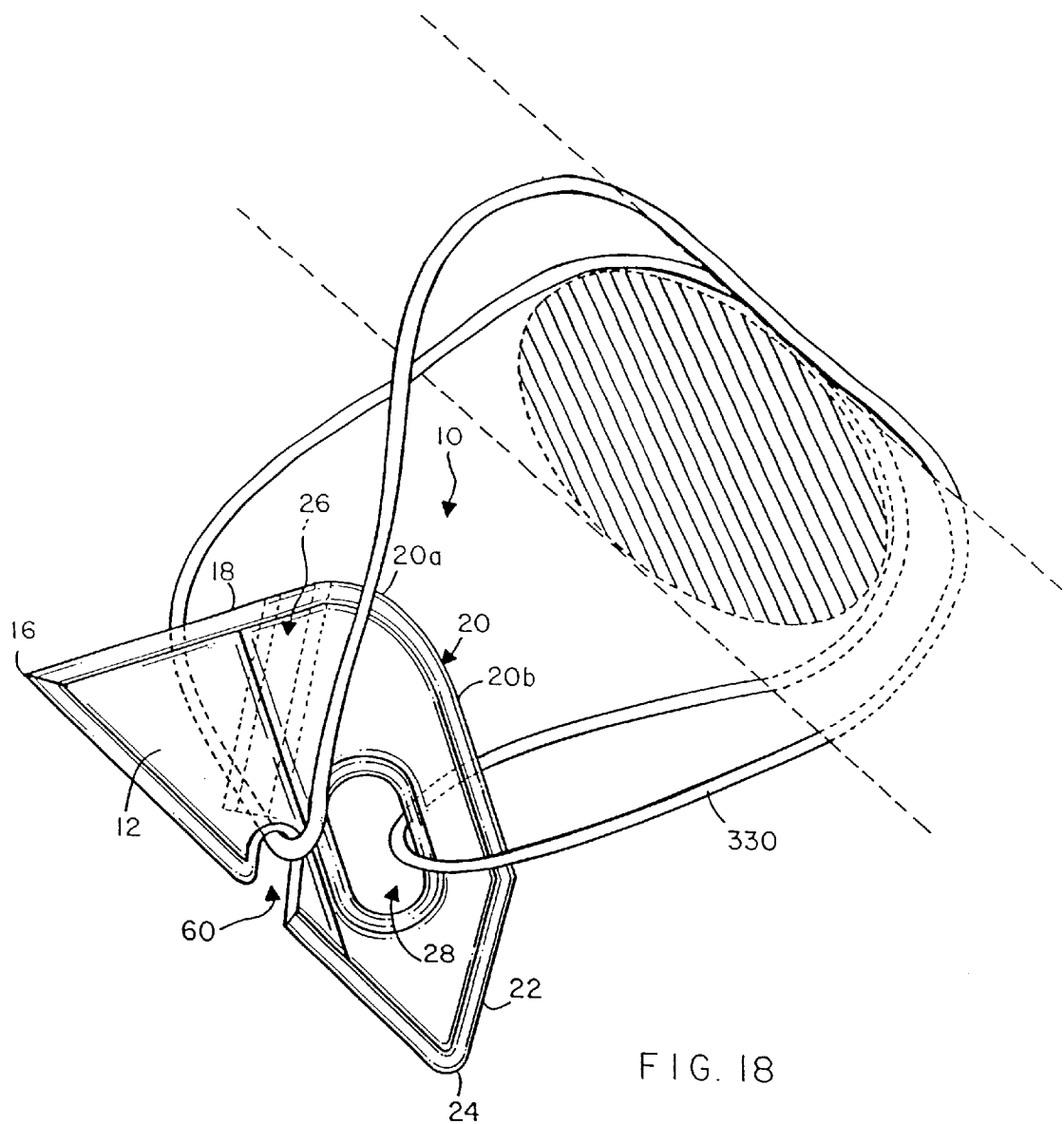
FIG. 18 shows an alternate embodiment of the present invention comprising a knotless suture anchor.

A further advantageous aspect of the present invention is shown in FIG. 18 and comprises an alternate embodiment of the present invention. While being similar to the embodiments previously described, the suture anchor 10 shown in FIG. 18 further includes a notch 60 angularly disposed in the bore-abutting surface 14 and extending into the body 12, wherein the location of the notch 60 along the bore-abutting surface 14 may vary. Where the suture anchor 10 also includes a suture 330 configured in the form of a loop, a knotless suture anchor 10 is provided. That is, the suture 330 may be wrapped about or otherwise engaged with the bodily tissue to be secured by the suture anchor 10 before it is wrapped about the suture anchor 10 to engage the notch 60. Once the suture 330 is engaged with the notch 60, the suture anchor 10 may be implanted into a bore in an adjacent bone according to the method previously described. On completion of the suture anchor 10 implantation procedure, the suture 330 is preferably not required to be further knotted since the bodily tissue is already secured to the adjacent bone.

Thus, embodiments of the present invention provide distinct advantages over the prior art. The leading gripping edge formed by the intersection of two surfaces provides a more robust structure than the tip of a cone, thereby providing a stronger suture anchor for high stress situations such as implantation of the anchor in high density bone. Further, the arcuate portion of the closing surface between the leading and trailing gripping edges facilitates rotation of the suture anchor in a bore in various bone structures, from dense cortical structures to less dense cancellous structures, thereby improving the seating ability of the suture anchor and requiring less effort to achieve the necessary rotation. In addition, the trailing gripping edge formed by the intersection of two surfaces provides a sharp gripping edge which is desirable in a dense bone structure. However, when included with the arcuate portion of the closing surface, the sharp trailing gripping edge permits the suture anchor to engage the bore in a less dense bone structure after the anchor has been rotated to provide the high seating surface area which is desirable for a less dense bone structure. Thus, the suture anchor according to embodiments of the present invention provides a mechanism for effectively anchoring a suture within a bore in a bone while also functioning equally in bones of differing densities, from hard dense bone to softer, less dense bone. Further, the uniform non-circular configuration of the inserter bore/insertion tool interface minimizes rotation of the suture anchor about the axis of the tip while facilitating a robust and easily connectable/disconnectable interface between the insertion tool and the suture anchor.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A kit for anchoring a suture in a bore in a bone, said kit comprising:
   at least one suture anchor for wedging within the bore and comprising:
      a non-conical body having a generally quadrilaterally shaped lateral cross-section, said body further having a bore-abutting surface having opposed ends and at least one gripping edge, the bore-abutting surface being adapted to abut a wall defining the bore upon insertion of the suture anchor into the bore;
      said body further defining:
         a suture bore extending transversely therethrough; and
         a non-circular inserter bore adapted to receive an insertion tool and disposed between the at least one gripping edge and the suture bore;
   at least one suture operably engaged with the suture bore, the suture passing through the suture bore and adapted to engage bodily tissue to be secured to the bone; and
   at least one insertion device for minimizing rotation of a suture anchor with respect to the insertion device and for implanting the suture anchor in the bore in the bone, comprising:
      a rigid shaft having opposed ends; and
      a tip at one end of said shaft, the tip being comprised of a shape memory material and having a proximal end operably engaged with the shaft and a free distal end capable of engagement with the inserter bore, the distal end of the tip having a non-circular cross-section corresponding to the non-circular cross-section of the inserter bore so as to minimize rotation of the suture anchor about the axis of the tip when the distal end of the tip is engaged with the inserter bore.

2. A kit according to claim 1 further comprising a leading surface intersecting the end of the bore-abutting surface last entering the bore at an acute angle so as to form a leading gripping edge such that the leading gripping edge has an edge width.

3. A kit according to claim 2 further comprising a trailing surface intersecting the end of the bore-abutting surface first entering the bore at an acute angle so as to form a trailing gripping edge.

4. A kit according to claim 3 further comprising a closing surface having an arcuate portion and a substantially linear portion, the arcuate portion engaging the leading surface and the substantially linear portion engaging the trailing surface so as to generally form a quadrilateral, the closing surface being disposed generally opposite the bore-abutting surface for facilitating the rotation of the body about the leading gripping edge within the bore.

5. A kit according to claim 2 wherein the inserter bore extends through the leading surface so as to be angularly disposed with respect to the bore-abutting surface.

6. A kit according to claim 2 wherein the leading surface is configured to be substantially planar.

7. A kit according to claim 2 wherein the leading surface defines a concave depression adjacent to the intersection of the leading surface with the bore-abutting surface.

8. A kit according to claim 2 wherein the leading surface is stepped between the inserter bore and the intersection of the leading surface with the bore-abutting surface.

9. A kit according to claim 2 wherein the leading surface and the bore-abutting surface both widen about the intersection thereof so as to increase the edge width of the leading gripping edge.

10. A kit according to claim 2 wherein the leading surface and the bore-abutting surface both narrow about the intersection thereof so as to decrease the edge width of the leading gripping edge.

11. A kit according to claim 2 wherein the inserter bore defines an axis extending toward the bore-abutting surface between the leading gripping edge and the suture bore.

12. A kit according to claim 1 further including at least one boring bit for forming a circular bore in the bone.

13. A kit according to claim 1 wherein the body is comprised of polylactic acid.

14. A kit according to claim 1 wherein the inserter bore is uniformly shaped along its length.

15. A kit according to claim 1 wherein the inserter bore is generally square.

16. A kit according to claim 1 wherein the tip is comprised of a nickel-titanium alloy.

17. A kit according to claim 1 wherein the tip is uniformly shaped along its length.

18. A kit according to claim 1 wherein the tip is generally square.

19. A kit according to claim 1 wherein the bore-abutting surface defines a notch therealong.

20. A kit according to claim 19 wherein the suture is configured to form a loop extending through the suture bore, the loop being further adapted to wrap about bodily tissue to be secured to the bone and then wrap about the body so as to engage the notch, before the suture anchor is inserted into the bore in the bone, to thereby cooperate with the suture anchor to form a knotless suture anchor.

* * * * *